(12) United States Patent
Jhung et al.

(10) Patent No.: US 7,855,299 B2
(45) Date of Patent: Dec. 21, 2010

(54) PREPARATION METHOD OF POROUS ORGANIC INORGANIC HYBRID MATERIALS

(75) Inventors: Sung-Hwa Jhung, Daejeon (KR); Jong-San Chang, Daejeon (KR); Young-Kyu Hwang, Daejeon (KR); Christian Serre, Versailles (FR); Gerard Ferey, Versailles (FR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 12/278,556

(22) PCT Filed: Feb. 7, 2007

(86) PCT No.: PCT/KR2007/000648

§ 371 (c)(1),
(2), (4) Date: Nov. 26, 2008

(87) PCT Pub. No.: WO2007/091828

PCT Pub. Date: Aug. 16, 2007

(65) Prior Publication Data

US 2009/0131703 A1    May 21, 2009

(30) Foreign Application Priority Data

Feb. 7, 2006   (KR) ..................... 10-2006-0011481

(51) Int. Cl.
   C07F 9/00    (2006.01)
   C07F 11/00   (2006.01)
   C07F 15/00   (2006.01)

(52) U.S. Cl. .............................. 556/44; 556/61; 556/147
(58) Field of Classification Search ............... 556/44, 556/61, 147
   See application file for complete search history.

(56) References Cited

U.S. PATENT DOCUMENTS

| 4,778,666 A | 10/1988 | Chu et al. |
| 2007/0012183 A1 | 1/2007 | Jhung et al. |
| 2009/0130411 A1* | 5/2009 | Chang et al. ............... 428/219 |
| 2009/0131643 A1* | 5/2009 | Ni et al. ......................... 534/16 |
| 2009/0227446 A1* | 9/2009 | Chang et al. ............... 502/167 |

FOREIGN PATENT DOCUMENTS

| CN | 1515490 A | 7/2004 |
| KR | 100627634 B1 | 9/2006 |
| KR | 1020060122576 A | 11/2006 |
| WO | 2007/035596 A2 | 3/2007 |
| WO | 2007/044473 A2 | 4/2007 |
| WO | 2007/102676 A1 | 9/2007 |
| WO | 2007/105871 A1 | 9/2007 |
| WO | 2008/057140 A2 | 5/2008 |
| WO | 2008/066293 A1 | 6/2008 |
| WO | 2008/072896 A1 | 6/2008 |

OTHER PUBLICATIONS

Ni et al., Journal of American Chemical Society, vol. 128, No. 38, pp. 12394-12395 (2006).*
Kim et al.; "Morphology Control of Organic-Inorganic Hybrid Mesoporous Silica by Microwave Heating," Chemistry Letters; 2004; pp. 422-423; vol. 33; No. 4.
Kitagawa et al.: "Functional Porous Coordination Polymers"; Angew. Chem. Int. Ed.; 2004; pp. 2334-2375; vol. 43.
James; "Metal-Organic Frameworks"; Chem. Soc. Rev., 2003; pp. 276-288; vol. 32.
Rosseinsky; "Recent Developments in Metal-Organic Framework Chemistry: Design, Discovery, Permanent Porosity and Flexibility"; Microporous and Mesoporous Materials; 2004; pp. 15-30; vol. 73.
Ferey et al.; "Crystallized Frameworks with Giant Pores: Are There Limits to the Possible?"; Accounts of Chemical Research; 2005; pp. 217-225; vol. 38; No. 4.
Di Renzo; "Zeolites as Tailor-Made Catalysts: Control of the Crystal Size"; Catalysis Today; 1998; pp. 37-40; vol. 41.
You et al.; "Liquid-Phase Catalytic Degradation of Polyethylene Wax Over MFI Zeolites with Different Particle Sizes"; Polymer Degradation and Stability; 2000; pp. 365-371; vol. 70.
Tosheva et al.; "Nanozeolites: Synthesis, Crystallization Mechanism, and Applications"; Chem. Mater.; 2005; p. 2494; vol. 17.
Hermes et al.; "Selective Nucleation and Growth of Metal-Organic Open Framework Thin Films on Patterned COOH/CF3-Terminated Self-Assembled Monolayers on AU(111)"; J. Am. Chem. Soc.; 2005; pp. 13744-13745; vol. 127.
Park et al.; "Supramolecular Interactions and Morphology Control in Microwave Synthesis of Nanoporous Materials"; Catalysis Surveys from Asia, Jun. 2004; pp. 91-110; vol. 8; No. 2.

(Continued)

*Primary Examiner* — Porfirio Nazario Gonzalez
(74) *Attorney, Agent, or Firm* — The Webb Law Firm

(57) ABSTRACT

The present invention relates to a synthesis method of porous hybrid inorganic-organic materials that can be applied for adsorbents, gas storages, sensors, membranes, functional thin films, catalysts, catalyst supports, encapsulating guest molecules and separation of molecules by the pore structures. More specifically, the present invention relates to the synthesis method of nanocrystalline porous hybrid inorganic-organic materials.

16 Claims, 2 Drawing Sheets

OTHER PUBLICATIONS

Ferey et al.; "A Chromium Terephthalate-Based Solid with Unusually Large Pore Volumes and Surface Area"; Science; 2005; 3 pages; vol. 309.

Jhung et al.; "Microwave Synthesis of a Nanoporous Hybrid Material, Chromium Trimesate"; Bulletin of the Korean Chemical Society; 2005; pp. 880-881; XP007910473; vol. 26, No. 6.

Ni et al.; "Rapid Production of Metal-Organic Frameworks via Microwave-Assisted Solvothermal Synthesis"; Journal of the American Chemical Society; 2006; pp. 12394-12395; XP009125576; vol. 128, No. 38.

Lin et al.; "Microwave-Assisted Synthesis of Anionic Metal-Organic Frameworks Under Ionothermal Conditions"; Chemical Communications; 2006; pp. 2021-2023; XP009125662; No. 19.

* cited by examiner

2theta/degree

PREPARATION METHOD OF POROUS ORGANIC INORGANIC HYBRID MATERIALS

TECHNICAL FIELD

The present invention relates to a preparation method of porous hybrid inorganic-organic material useful as adsorbents, gas storages, catalysts, catalyst supports, carriers and templates for nanomaterials and electronic and electric materials. More particularly, present invention relates to a preparation method of porous hybrid inorganic-organic material, with particle size less than 500 nm, by using microwave heating rather than conventional electric heating as a heat source for a hydrothermal or solvothermal synthesis.

BACKGROUND ART

The porous hybrid inorganic-organic materials that are explained in this invention are defined as inorganic-organic coordination polymers composed of central metallic ions and organic ligands coordinated to the metal ions. The porous hybrid inorganic-organic materials are crystalline materials having porous structures with the pore sizes of molecules or nanometers, and the framework structures of porous hybrid inorganic-organic materials are composed of both organic materials and inorganic species. The porous hybrid inorganic-organic material is wide terminology and also can be called as porous coordination polymer (Angew. Chem. Intl. Ed., 43, 2334. 2004) or metal-organic framework (Chem. Soc. Rev., 32, 276, 2003). The studies on these materials have been recently developed by the combination of coordination chemistry and materials science. These materials are widely studied because they have many applications such as adsorbents, gas storages, sensors, membranes, functional thin films, catalysts and catalyst supports due to high surface area and pores of size of molecules or nanometers. Moreover, they can be used to encapsulate molecules or separate molecules depending on the sizes of molecules. These porous hybrid inorganic-organic materials can be synthesized by several methods including solvent-diffusion method, hydrothermal synthesis using water as solvent and a solvothermal synthesis using an organic solvent (Microporous Mesoporous Mater., 73, 15, 2004; Accounts of Chemical Research, 38, 217, 2005).

The synthesis of porous hybrid inorganic-organic materials can be executed, similar to the synthesis of inorganic porous materials including zeolites and mesoporous materials, under autogenous pressure in the presence of water or suitable solvents at zeolites and mesoporous materials, during several days at high temperature after loading reactants in a high pressure reactor such as an autoclave. The heat source for high temperature has generally been electric or resistive heating. For example, an autoclave containing precursors including metal salts, organic ligands and water or solvent was heated using an electric heater or an electric oven at a constant temperature. However, the methods of the previous embodiments have drawbacks of using excessive energy because the nucleation or crystallization is very slow. Moreover, the methods are very inefficient because the synthesis can be carried out only by batch reactions (Accounts of Chemical Research, 38, 217, 2005). The previous synthesis methods are considered as inefficient methods to implement commercial applications because of high production cost.

Moreover, it is known that porous catalytic materials with small particle size have advantages of increased activity and facile regeneration of used catalysts because diffusivity increases with decreasing the crystal size of catalysts (Catalysis Today, 41, 37, 1998; Polymer Degradation and Stability 70, 365, 2000). Moreover, nanocrystalline porous materials have many applications in the fields of sensors, opto-electronics and medicines (Chem. Mater., 17, 2494, 2005). However, it is not easy to synthesize small crystals, and so-called nanoparticles smaller than 100 nm is especially difficult to obtain because of easy aggregation or coagulation. Carbon or polymer templates may be used to synthesize nanoparticles even though the synthesis process is complex. However, it is not easy to obtain pure nanoparticles without a template because small particles grow easily to a big size when the template is removed.

Moreover, it is necessary to prepare porous hybrid inorganic-organic materials with homogeneous particle size and membrane or thin film of the materials for the applications in sensors or opto-electronic devices. In a previous method, membranes or thin films were made by two steps of synthesizing and making a simple composite by impregnation of porous hybrid inorganic-organic materials on a polymer. However, the process is complex and it is difficult to apply for insoluble porous hybrid inorganic-organic materials. Another method using a gold plate on which an organic functional group is anchored is reported; however, the method is complicated due to the anchoring and recrystallization (Journal of the American Chemical Society, 127, 13744, 2005).

Hence, it is an object of the present invention to provide a new preparation method of a porous hybrid inorganic-organic material and, especially nanocrystalline porous hybrid inorganic-organic material including thin film or membrane.

On the other hand, there have been mass production methods such as hydrothermal crystallization for inorganic porous materials including zeolites because they have been used for 50 years or so in the petrochemistry or refinery. However, the general hydrothermal method using electric heating is ineffective due to long crystallization time. Therefore, since 1988, microwave heating has been suggested to increase the efficiency or productivity in the synthesis of inorganic porous materials (U.S. Pat. No. 4,778,666; Catal. Survey Asia, 8, 91, 2004). It was reported that synthesis time could be decreased by using microwave heating compared with conventional electric heating, and continuous synthesis was also reported for a few cases using microwave heating. However, the synthesis mechanisms of porous hybrid inorganic-organic materials are very different to that of inorganic porous materials. Organic molecules do not remain or incorporated in an inorganic porous material because organic molecules are removed by calcination after synthesis even though some organic amines or ammonium salts are used as templating molecules in the synthesis of inorganic porous materials. On the other hands, organic molecules construct a framework structure of porous hybrid inorganic-organic materials. In aminorganic porous material, oxygen atoms link a metal and another metal, whereas ligand, derived from an organic molecule, connects metal species. Therefore, the synthesis of porous hybrid inorganic-organic materials has been accomplished by using electric heating only because the synthesis is just at the beginning stage of development (Science, 2005, 309, 2040). Therefore, there have been few attemptsto synthesize a porous hybrid inorganic-organic material by using microwave heating.

Recently, the synthesis of porous hybrid inorganic-organic materials by using microwave irradiation, after adequatepretrements, has been reported by the present inventors (Kor. Pat. Application 2005-0045153); however, there has been no report on the crystal size control or the synthesis of nanocrystalline porous hybrid inorganic-organic materials.

Moreover, to synthesize nanocrystalline porous hybrid inorganic-organic materials, preferably in a short reaction time, and more preferably in a continuous reaction mode, is very important for commercial applications of porous hybrid inorganic-organic materials in catalysts, catalyst supports, adsorbents, ion exchangers, magnetic materials, thin films, gas storages, nanoreactors and nanosciences such as storage, preparation and separation of nanomaterials.

DISCLOSURE OF INVENTION

Technical Problem

The present inventors have made intensive researches to fulfill the targets described above, and as a result, found a novel synthesis method of porous hybrid inorganic-organic materials in which microwave irradiation is used as a heat source. The present method is directed to synthesize porous hybrid inorganic-organic materials, in more environment-friendly way and in increased energy efficiency, with nanocrystalline morphology.

Accordingly, the object of this invention is to provide a process for producing nanocrystalline porous hybrid inorganic-organic materials that have many applications in an economical and environment-friendly way, especially in a short reaction time. Moreover, this invention is also to provide a method for producing a thin film or membrane of porous hybrid inorganic-organic materials by the direct microwave irradiation in one step.

Technical Solution

The present invention is directed to a novel process for preparing nanocrystalline porous hybrid inorganic-organic materials by utilizing microwave irradiation as a heat source of a hydrothermal or solvothermal reaction.

The present invention, providing porous hybrid inorganic-organic materials with particle size of 500 nm or less, includes following steps in the preparation.

1) the step to prepare reactant mixtures by mixing metal precursors, organic molecules that can be used as ligands and solvent; and 2) the step to heat the reactant mixtures higher than 100° C. by irradiation of microwave with the frequency of 0.3-300 GHz The porous hybrid inorganic-organic materials obtained by the present method are powder, thin film or membrane in shape.

The porous hybrid inorganic-organic materials in thin film or membrane are easily prepared from the reactant mixtures by microwave irradiation after dipping a substrate in the reactant mixtures.

The present invention provides a preparation method of porous hybrid inorganic-organic materials which have regular pore size of nanometers and the average particle size less than 500 nm, preferably less than 200 nm, and more preferably less than 100 nm and most preferably less than 50 nm.

The present invention will be described in more detail as follows:

The present invention utilizes microwave irradiation rather than conventional electric heating as a heat source for high temperature reaction. The microwaves described in this invention are any microwaves that have frequency of 300 MHz-300 GHz. The commercially available microwaves with frequency of 2.45 GHz or 0.915 GHz are convenient and effective to use in the invention.

The metallic species, one of the components of porous hybrid inorganic-organic materials, can be any metallic materials such as Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, Mg, Ca, Sr, Ba, Sc, Y, Al, Ga, In, Tl, Si, Ge, Sn, Pb, As, Sb, and Bi. Transition metals, to make a coordination compound easily, are suitable for the invention. Among transition metals, Cr, Ti, V, Mn, Fe, Co, Ni and Cu are more suitable, and Cr is most suitable. Main group elements which makea coordination compound easily and lanthanides can also be used as a metal component. Al and Si are suitable metallic components among main group elements, whereas Ce and La are suitable elements among lanthanides. As metallic precursors, metals themselves and any compounds containing metallic components can be used.

Any organic molecules are suitable as another component of a porous hybrid inorganic-organic material as long as the molecules contain functional groups that can coordinate to a metal center. The functional groups that can coordinate to a metal are carboxylic acid, carboxylate, amino (—NH$_2$),

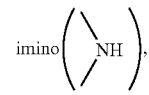

amide (—CONH$_2$), sulfonic acid (—SO$_3$H), sulfonate (—SO$_3^-$), methanedithionic acid (—CS$_2$H), methanedithionate (—CS$_2^-$), pyridine, pyrazine, etc. Multidentates, having multiple coordinating sites, such as bidentates and tridentates are suitable for preparing stable porous hybrid inorganic-organic materials. Any organicmolecules can be used irrespective of the charges such as cationic, anionic and neutral compounds as long as they have coordination sites. For example, neutral molecules such as bipyridine and pyrazine and anionic molecules such as terephthalate, naphthalenedicarboxylate, benzenetricarboxylate, glutarate and succinate can be used.

Ions containing aromatic rings such as terephthalate, ions without aromatic rings such as formate, and ions containing non-aromatic rings such as cyclohexyldicarboxylate are suitable for carboxylate anions. Not only organic species containing coordination sites but also organic species containing potential sites that can be transformed into a state suitable for coordination under the reaction conditions are applicable to organic precursors. For example, organic acids such as terephthalic acid can be used because it can be converted to terephthalate to coordinate to a metal center under reaction conditions. Typical organic species are benzenedicarboxylic acids, naphthalenedicarboxylic acids, benzenetricarboxylic acids, naphthalenetricarboxylic acids, pyridinedicarboxylic acids, bipyridyldicarboxylic acids, formic acid, oxalic acid, malonic acid, succinic acid, glutaric acid, hexanedionic acid, heptanedionic acid, cyclohexyldicarboxylic acids, etc. Anions of the above described acids are also suitable. Pyrazine and bipyridines are neutral species that can be applied as organic ligands. Mixtures of two or more of the above mentioned organic moieties are also applicable.

Chromium terephthalate, vanadium terephthalate and iron terephthalate are typical examples of porous hybrid inorganic-organic materials, and chromium terephthalate is one of the well-known porous hybrid inorganic-organic materials. Cubic chromium terephthalate with huge surface area and large pore size has great commercial interest.

Instead of metallic components and organic ligands, suitable solvents are necessary for the synthesis of porous hybrid inorganic-organic materials. As the solvents, water, alcohols such as methanol, ethanol and propanol, and ketones such as acetone and methylethyl ketone and hydrocarbons such as hexanes, heptanes and octanes are suitable. Mixtures of above solvents can be applied and water is the most suitable solvent.

The reaction temperature does not have any practical limitation. However, temperature above 100° C. is suitable, and temperature of 100-250° C. is more suitable, and temperature of 150-220° C. is most suitable. When the reaction temperature is too low, the reaction rate is too slow and the productivity is too low, whereas when the temperature is too high, dense species without pore is obtained and impurities can be byproduced because the reaction rate is too high. Moreover, it is costly to construct a reactor for high pressure reaction when the reaction temperature is too high. The reaction pressure does not have any limitation. It is convenient to perform a reaction under the autogenous pressure at the reaction temperature. Moreover, the reaction can be performed under higher pressure by adding inert gases such as nitrogen or helium.

The reaction can be carried out both in a batch mode and in a continuous mode. The batch mode operation is suitable for production in small scale because the throughput per time is low, whereas continuous mode is suitable for mass production of porous hybrid inorganic-organic materials even though investment cost is high. The reaction time of batch mode operation is from 1 min to 8 h. When the reaction time is too long, byproducts are mixed in the product and it is hard to get nanoparticles because of crystal growth. On the contrary, the conversion is low when the reaction time is too short. Reaction time of 1 min-60 min is more suitable. The residence time of 1 min-60 min is suitable for a continuous reaction. When the residence time is too long, byproducts are mixed in the product and it is hard to get nanoparticles. The throughput per time is low when the residence time is long. On the contrary, reaction conversion is low when the residence time is short. The residence time of 1 min-20 min is more suitable. During the batch-mode reaction, the reactant mixtures can be agitated, and the agitation speed of 100-100 rpm is suitable. The reaction can be performed statically and the static reaction is more suitable because of low investment cost and easy operability.

It is advisable to irradiate microwaves on pretreated reactant mixtures because the reaction using microwaves is very fast and homogeneous or nucleated reaction mixtures are suitable for the reaction. When the microwaves are irradiated on reaction mixtures without a pretreatment, the reaction rate is low or impurities may be mixed in or the crystal sizes can be inhomogeneous even though the process will be simple.

The pretreatment can be accomplished either by treatment using ultrasonics or by vigorous mixing. The pretreatment temperature is suitable between room temperature and the reaction temperature. If the pretreatment temperature is too low, the pretreatment effect is too small, whereas if the pretreatment temperature is too high, the equipment for pretreatment is complex and impurities may be by produced. Pretreatment time longer than 1 min is suitable. Pretreatment time between 1 min and 5 h is more suitable for the ultrasonic treatment, whereas pretreatment for 5 min or more is more suitable for the vigorous stirring. If the pretreatment time is too short, the pretreatment effect is too small, whereas if the pretreatment time is too long, the efficiency of pretreatment is low. Pretreatment using ultrasonics is effective in pretreatment time and homogeneity of the reactant mixtures.

The membrane or thin film of porous hybrid inorganic-organic materials can be made by microwave irradiation after dipping a substrate in the reaction mixtures-mentioned above. The substrate can be alumina, silicon, glass, indium tin oxide (ITO), indium zinc oxide (IZO) and heat-resistant polymers. Any surface-treated substrate mentioned above will be more suitable.

BRIEF DESCRIPTION OF THE DRAWINGS

FIG. 3a and FIG. 3b are obtained from Examples 2 and 3, respectively.

MODE FOR THE INVENTION

The following specific examples are intended to be illustrative of the invention and should not be construed as limiting the scope of the invention as defined by appended claims.

Example 1

Cr-BDCA-1

Figure 1:
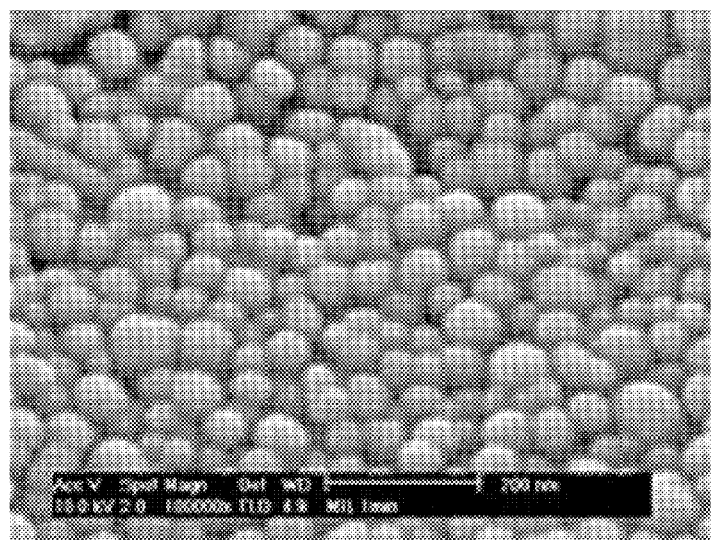
FIG. 1 represents the scanning electron microscopes of chromium terephthalate, obtained in Example 1.

Reactant mixtures with the molar composition of Cr:HF:BDCA:$H_2O$=1:1:1:275 were prepared from Cr($NO_3$)$_3$.9$H_2O$, aqueous HF, 1,4-benzenedicarboxylic acid (BDCA) and water. The reactant mixtures were loaded in a Teflon reactor, and pretreated by ultrasonic wave treatment for 1 min in order to homogenize the mixture and facilitate the nucleation. The Teflon reactor containing pretreated reactant mixtures was put in a microwave oven (CEM, Mars-5). The synthesis was carried out under microwave irradiation (2.45 GHz) for 1 min at 210° C. after the reaction temperature was reached for 3 min under microwave irradiation. The porous hybrid inorganic-organic material, chromium terephthalate, Cr-BDCA-1 was recovered by cooling to room temperature, centrifugation, washing with deionized water and drying. It was confirmed that a cubic chromium terephthalate was obtained by the XRD result to show characteristic diffraction peaks at 3.3, 5.2, 5.9, 8.5 and 9.1 (2θ). The SEM (scanning electron microscope) image of Cr-BDAC-1 obtained in this example is shown in FIG. 1, and shows that the crystals are 30-40 nm and very homogeneous in size. These results show that a porous hybrid inorganic-organic material can be obtained very efficiently in a short reaction time by adequate pretreatment and microwave irradiation.

Example 2

Cr-BDCA-2

Figure 3:
FIG. 3 represents the X-ray diffraction patterns of chromium terephthalate, obtained in Examples.
Figure 3:
Figure 3:
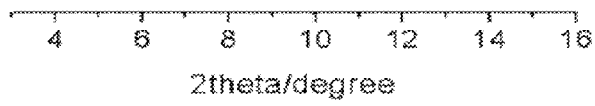
Figure 4:
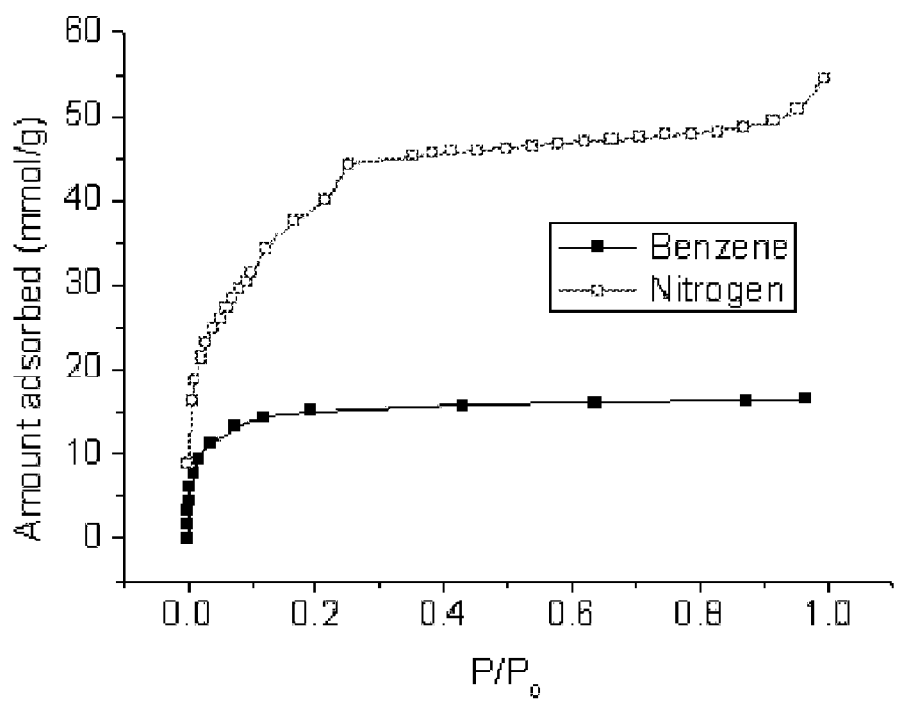
FIG. 4 represents the adsorption isotherms of nitrogen and benzene of chromium terephthalate, obtained in Example 2.

The synthesis of a porous hybrid inorganic-organic material was carried out as Example 1, except that ultrasonic pretreatment was omitted and the reaction time was 2 min. X-ray diffraction patterns of FIG. 3a show that a material with structure same as Example 1 was obtained, and SEM image confirms that a porous hybrid inorganic-organic material with homogeneous size of 40-50 nm was obtained. The porous hybrid inorganic-organic material, after evacuation at 150° C., has nitrogen adsorption capacity of 1050 mL/g or 46.9 mmol/g at relative pressure of 0.5 (P/Po=0.5, at liquid nitrogen temperature). Moreover, the porous hybrid inorganic-organic material has high benzene adsorption capacity (16 mmol/g) at 30° C. and relative pressure of 0.5 (P/Po=0.5). The adsorption isotherms of nitrogen and benzene are shown in FIG. 4. Therefore, the nanocrystalline porous hybrid inorganic-organic material, chromium terephthalate, synthesized in this example has very high adsorption capacity to be used successfully as adsorbents, catalysts, catalyst supports, etc.

Example 3

Cr-BDCA-3

Figure 2:
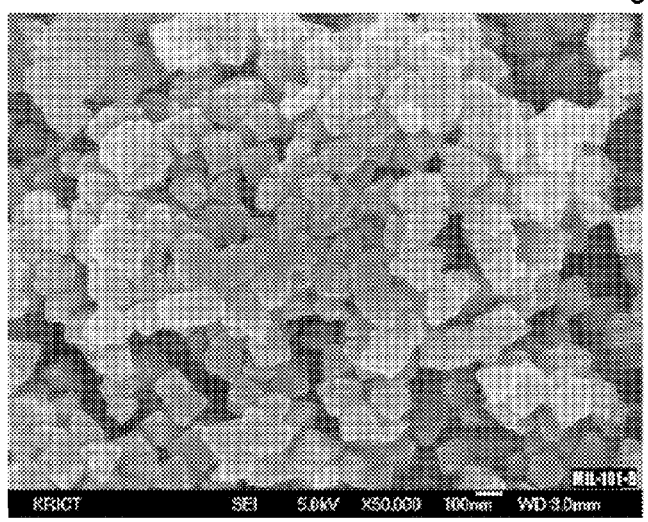
FIG. 2 represents the scanning electron microscopes of chromium terephthalate, obtained in Example 3.

The synthesis of a porous hybrid inorganic-organic material was carried out as Example 2, except that the reaction time was 40 min. X-ray diffraction patterns of FIG. 3b show that a material with structure same as Example 1 was obtained, and SEM image (FIG. 2) confirms that a porous hybrid inorganic-organic material with homogeneous size of 200 nm was obtained even though the crystal size increased considerably compared with the size of Example 2.

Example 4

Fe-BDCA-1

The synthesis of a porous hybrid inorganic-organic material was carried out as Example 2, except that $FeCl_3$ was used instead of $Cr(NO_3)_3.9H_2O$. X-ray diffraction patterns showed that a material with structure same as Example 1 was obtained, and SEM image confirmed that a porous hybrid inorganic-organic material with homogeneous size of 50-100 nm was obtained.

Example 5

V-BDCA-1

The synthesis of a porous hybrid inorganic-organic material was carried out as Example 2, except that $VCl_3$ was used instead of $Cr(NO_3)_3.9H_2O$. X-ray diffraction patterns showed that a material with structure same as Example 1 was obtained, and SEM image confirmed that a porous hybrid inorganic-organic material with homogeneous size of 50-80 nm was obtained.

Example 6

Cr-BDCA-1 Thin Film

Figure 5:
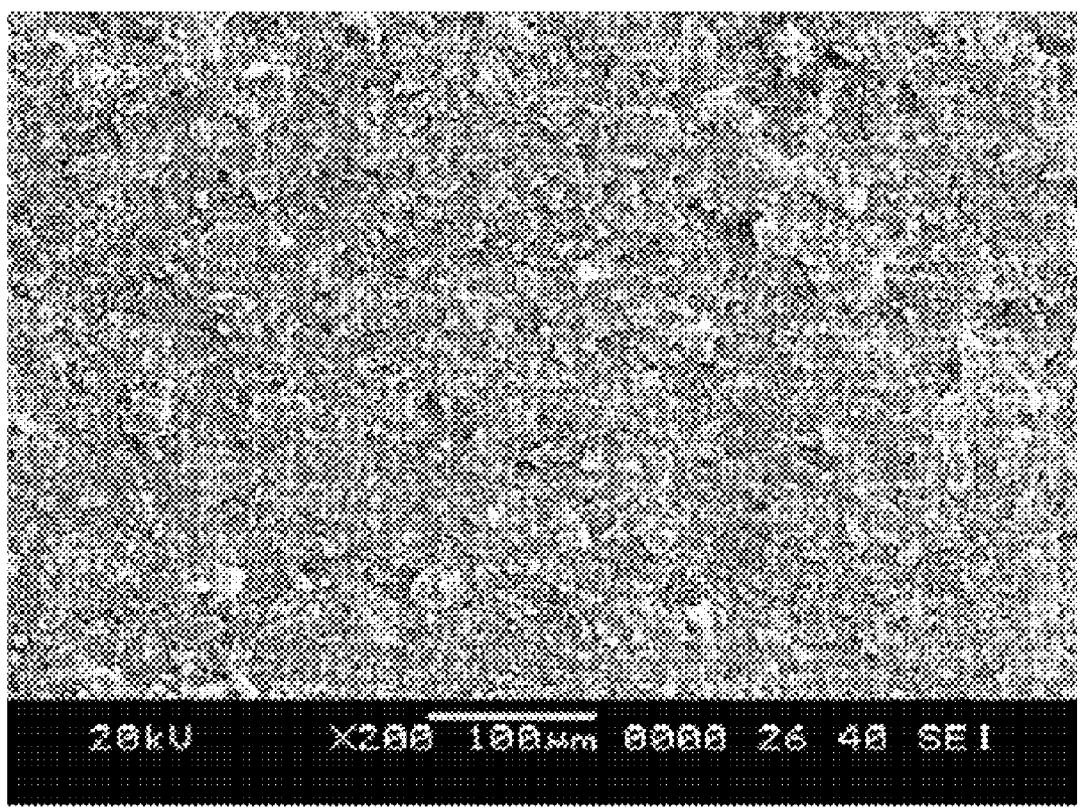
FIG. 5 represents the scanning electron microscope of chromium terephthalate thin film, obtained in Example 6.

Reactant mixtures with the molar composition of Cr:HF:BDCA:$H_2O$=1:1:1:275 were prepared from $Cr(NO_3)_3.9H_2O$, aqueous HF, 1,4-benzenedicarboxylic acid (BDCA) and water. The reactant mixtures were loaded in a Teflon reactor, and an alumina plate was aligned vertically in the reactant mixture. The Teflon reactor containing reactant mixtures and alumina plate was put in a microwave oven (CEM, Mars-5). The synthesis was carried out under microwave irradiation (2.45 GHz) for 30 min at 210° C. after the reaction temperature was reached for 3 min under microwave irradiation. The porous hybrid inorganic-organic material, chromium terephthalate, Cr-BDCA-1 (both powder and thin film) was recovered by cooling to room temperature, centrifugation, washing with deionized water and drying. The XRD patterns of the thin film were very similar to those of experiment 1. The SEM image of the thin film is shown in FIG. 5, and illustrates that the thin film, Cr-BDCA/alumina, is coated homogeneously with small particles. These results show that a porous hybrid inorganic-organic material thin film can be obtained directly and efficiently in a short reaction time by microwave irradiation.

Comparative Example 1

Cr-BDCA-4

The synthesis of a porous hybrid inorganic-organic material was carried out as Example 2, except that conventional electric oven was used instead of a microwave oven, and the reaction temperature and time was 220° C. and 10 h, respectively. X-ray diffraction patterns showed that a material with structure same as Example 1 was obtained. However, SEM image showed that a porous hybrid inorganic-organic material with big size of 1000-2000 nm was obtained. Moreover, the crystal size was not homogeneous.

Comparative Example 2

Cr-BDCA-4

The synthesis of a porous hybrid inorganic-organic material was carried out as Comparative Example 1, except that the reaction time was 2 h. X-ray diffraction patterns showed that amorphous material was obtained rather than a crystalline material.

From the Comparative Examples, it can be known that to synthesize a nanocrystalline porous hybrid inorganic-organic material with size less than 500 nm is impossible by using conventional electric heating. Moreover, synthesis method using microwave irradiation has the advantage of rapid, economical and effective preparation of nanocrystalline porous hybrid inorganic-organic material.

INDUSTRIAL APPLICABILITY

As described above, the synthesis of porous hybrid inorganic-organic material by using microwave irradiation has the advantage of reduction of reaction time, energy saving, high productivity. Therefore, the synthesis method in this invention can be competitive method in the point of environment and economics. Especially, the synthesis of nanocrystalline porous hybrid inorganic-organic material, less than 500 nm, is fulfilled by microwave synthesis. Moreover, a thin film and membrane can be easily fabricated directly. This porous hybrid inorganic-organic material has the applications such as catalysts, catalyst supports, adsorbents, gas storages, ion exchangers, nanoreactors and templates or carriers of nanomaterials. The nanocrystalline porous hybrid inorganic-organic materials can be used in active catalysts, sensors, opto-electronic materials and medical materials.

The invention claimed is:
1. A preparation method of porous hybrid inorganic-organic materials with size smaller than 500 nm, comprising:
   1) the step to prepare reaction mixtures by mixing metal precursors, organic compounds that can be used as ligands and solvent; and
   2) the step to irradiate microwave on the reaction mixtures prepared as above and to heat.
2. The preparation method of porous hybrid inorganic-organic materials according to claim 1, wherein metal precursors are one or more of metals selected from Ti, Zr, Hf, V,

Nb, Ta, Cr, Mo, W, Mn, Re, Fe, Ru, Os, Co, Rh, Ti, Ni, Pd, Pt, Cu, Ag, Au, Zn, Cd, Hg, Mg, Ca, Sr, Ba, Sc, Y, Al, Ga, In, Ti, Si, Ge, Sn, Pb, As, Sb, or Bi; or metal compounds containing one or more components selected from Ti, Zr, Hf, V, Nb, Ta, Cr, Mo, W, Mn, Re, Fe, Ru, Os, Co, Rh, Ti, Ni, Pd, Pt, Cu, Ag, Au, Zn, Cd, Hg, Mg, Ca, Sr, Ba, Sc, Y, Al, Ga, In, Ti, Si, Ge, Sn, Pb, As, Sb, or Bi.

3. The preparation method of porous hybrid inorganic-organic materials according to claim 1, wherein the organic compounds are the molecules or molecular mixtures containing one or more of the functional groups selected from carboxylic acid, carboxylate, amino (—NH$_2$),

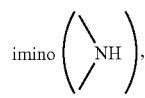

amide (—CONH$_2$), sulfonic acid (—SO$_3$H), sulfonate (—SO$_3$), methanedithionic acid (—CS$_2$H), methaneditbionate (—CS$_2$), pyridine or pyrazine.

4. The preparation method of porous hybrid inorganic-organic materials according to claim 3, wherein the organic compounds containing carboxylic functional groups are selected from benzenedicarboxylic acids, naphthalenedicarboxylic acids, benzenetricarboxylic acids, naphthalenetricarboxylic acids, pyridinedicarboxylic acids, bipyridyldicarboxylic acids, formic acid, oxalic acid, malonic acid, succinic acid, glutaric acid, hexanedionic acids, heptanedionic acids and cyclohexyidlicarboxylic acids.

5. The preparation method of porous hybrid inorganic-organic materials according to claim 1, wherein the reaction temperature is 100-250° C.

6. The preparation method of porous hybrid inorganic-organic materials according to claim 5, wherein the reaction temperature is 150-220° C.

7. The preparation method of porous hybrid inorganic-organic materials according to claim 1, wherein the reaction is carried out by using a batch reactor or a continuous reactor.

8. The preparation method of porous hybrid inorganic-organic materials according to claim 1, wherein the reaction mixtures are treated additionally by ultrasonic treatment for 1 min or more or by agitation for 5 min or more between Step 1 and Step 2.

9. The preparation method of porous hybrid inorganic-organic materials according to claim 1, wherein the average particle size of porous hybrid inorganic-organic materials is less than 200 nm.

10. The preparation method of porous hybrid inorganic-organic materials according to claim 9, wherein the average particle size of porous hybrid inorganic-organic materials is less than 100 nm.

11. The preparation method of porous hybrid inorganic-organic materials according to claim 10, wherein the average particle size of porous hybrid inorganic-organic materials is less than 50 nm.

12. The preparation method of porous hybrid inorganic-organic materials according to claim 1, wherein the porous hybrid inorganic-organic material is one selected from chromium terephthalate, iron terephthalate or vanadium terephthalate.

13. The preparation method of porous hybrid inorganic-organic materials according to claim 12, wherein the porous hybrid inorganic-organic material is chromium terephthalate.

14. The preparation method of porous hybrid inorganic-organic materials according to claim 13, wherein the porous hybrid inorganic-organic material is a cubic chromium terephthalate that has pores.

15. The preparation method of porous hybrid inorganic-organic materials according to claim 1, wherein the porous hybrid inorganic-organic materials are states of thin films or membranes.

16. The preparation method of porous hybrid inorganic-organic materials according to claim 15, wherein the porous hybrid inorganic-organic materials in thin films or membranes are prepared by dipping alumina, silicon, glass, indium tin oxide (ITO), indium zinc oxide (IZO) or heat resistant polymers in the reactant mixtures.

* * * * *